United States Patent
Yamaguchi et al.

(10) Patent No.: US 11,960,149 B2
(45) Date of Patent: Apr. 16, 2024

(54) MEASUREMENT METHOD FOR VISUAL BEHAVIOR, DESIGN METHOD AND MANUFACTURING METHOD FOR PROGRESSIVE POWER LENS

(71) Applicant: HOYA LENS THAILAND LTD., Pathumthani (TH)

(72) Inventors: Eiichiro Yamaguchi, Tokyo (JP); Toshiaki Sonehara, Tokyo (JP); Ayumu Ito, Tokyo (JP)

(73) Assignee: HOYA LENS THAILAND LTD., Pathumthani (TH)

( * ) Notice: Subject to any disclaimer, the term of this patent is extended or adjusted under 35 U.S.C. 154(b) by 185 days.

(21) Appl. No.: 17/491,018

(22) Filed: Sep. 30, 2021

(65) Prior Publication Data
US 2022/0100001 A1 Mar. 31, 2022

(30) Foreign Application Priority Data
Sep. 30, 2020 (JP) ................. 2020-164772

(51) Int. Cl.
*G02C 7/02* (2006.01)
*G02C 7/06* (2006.01)

(52) U.S. Cl.
CPC ............. *G02C 7/027* (2013.01); *G02C 7/061* (2013.01)

(58) Field of Classification Search
CPC ........ G02C 7/027; G02C 7/061; G02C 7/025; G02C 13/005; A61B 3/113
See application file for complete search history.

(56) References Cited

U.S. PATENT DOCUMENTS

| 2005/0088616 A1* | 4/2005 | Nason ................. G02C 7/027 351/159.74 |
| 2011/0116038 A1* | 5/2011 | Suzuki ................. G02C 7/027 351/159.75 |
| 2011/0128496 A1* | 6/2011 | Giraudet ............. G02C 7/027 351/204 |

(Continued)

FOREIGN PATENT DOCUMENTS

| EP | 1 959 294 A2 | 8/2008 |
| EP | 3 686 656 A1 | 7/2020 |

(Continued)

OTHER PUBLICATIONS

May 9, 2022 Search Report issued in European Patent Application No. 21199329.0.

*Primary Examiner* — Darryl J Collins
*Assistant Examiner* — Matthew Y Lee
(74) *Attorney, Agent, or Firm* — Oliff PLC (57) ABSTRACT

Provided is technology that makes it possible to measure visual behavior with respect to objects that are at different distances in the depth direction, while reducing burden on a subject. A method for measuring visual behavior of a subject to design an eyeglass lens includes: a step (a) of ascertaining a head rotation amount that is generated by the subject in a sagittal plane of the subject when gazing at each of a plurality of gaze points that are set at predetermined distances different from each other in a forward depth direction; and a step (b) of determining an eyeball rotation amount that is generated by the subject when gazing at each of the plurality of gaze points, based on the head rotation amount.

9 Claims, 7 Drawing Sheets

(56) References Cited

U.S. PATENT DOCUMENTS

| | | | |
|---|---|---|---|
| 2015/0103312 A1* | 4/2015 | Paille | G02C 7/025 351/204 |
| 2015/0309338 A1* | 10/2015 | Chauveau | G02C 7/027 351/204 |
| 2016/0011437 A1* | 1/2016 | Nishimura | A61B 3/113 351/204 |
| 2018/0303336 A1 | 10/2018 | Escalier et al. | |
| 2019/0324290 A1* | 10/2019 | El-Hajal | G02C 7/06 |
| 2022/0113563 A1* | 4/2022 | Baranton | G02C 13/005 |

FOREIGN PATENT DOCUMENTS

| | | |
|---|---|---|
| JP | 2014-195647 A | 10/2014 |
| JP | 2018-531706 A | 11/2018 |

* cited by examiner

FIG. 1

S102 Gaze point arrangement step
S103 Head rotation amount ascertainment step
S104 Eyeball rotation amount ascertainment step

S102 Gaze point arrangement step
S103 Head rotation amount ascertainment step
S104 Eyeball rotation amount ascertainment step
S105 Visual behavior judgement step

S102 Gaze point arrangement step
S103 Head rotation amount ascertainment step
S104 Eyeball rotation amount ascertainment step
S105 Visual behavior judgement step
S106 Correction method determination step

MEASUREMENT METHOD FOR VISUAL BEHAVIOR, DESIGN METHOD AND MANUFACTURING METHOD FOR PROGRESSIVE POWER LENS

BACKGROUND OF THE INVENTION

1. Field of the Invention

The present invention relates to a measurement method for visual behavior, a design method and a manufacturing method for a progressive power lens.

2. Description of Related Art

It has been proposed that an eyeglass lens be designed considering visual behavior of a wearer. For example, JP 2014-195647A discloses a line-of-sight detection device with which it is possible to precisely measure a line of sight in a wide field of view by not only performing calibration based on a measurement result of eyeball movement when visual targets are gazed at in order by only moving eyeballs without moving the head, but also performing calibration based on a measurement result of eyeball movement when a line-of-sight direction is changed by moving the head while gazing at a predetermined visual target, and discloses designing an eyeglass lens based on an analysis result of gaze points and transmission points obtained using the line-of-sight detection device in which the calibration method is used.

Also, JP 2018-531706A discloses a method and a test device with which it is possible to measure a parameter of natural visual behavior of an individual easily and accurately, with consideration given to a posture assumed by the individual while reading, and focusing on near vision, which is important particularly in optical design of a progressive power eyeglass lens.

JP 2014-195647A and JP 2018-531706A are examples of related art.

SUMMARY OF THE INVENTION

According to JP 2014-195647A, a subject is required to wear a head band to which at least a forward visual field camera, an eyeball camera, an infrared LED, and a dichroic mirror are attached, and, in order to carry out the described calibration, the subject is required to move his head such that the line-of-sight direction is distributed over an angular range as wide as possible in the up-down direction and the left-right direction so as to encompass viewing angles to be measured, and such that a line of sight of the visual target does not go out of an eyeglass lens or is not interrupted by the frame of the eyeglass, the nose of the subject, or the like.

Also, the line-of-sight direction is restricted in the calibration procedure, and therefore, the subject is required to make unnatural movement when compared with movement for seeing the visual target by merely wearing the eyeglass. JP 2014-195647A further describes performing measurement for calibration a plurality of times by changing the distance between the subject and the visual target, but this is for incorporating a difference from a distance at which measurement is to be performed in actual detection of the line of sight into the conversion, the difference being generated due to movement of the head during calibration, and does not mean that there are a plurality of distances at which measurement is to be performed. In common detection of the line of sight, if the distance to an object changes in the depth direction, the change appears as parallax (mismatch of detection point) between left and right views, and therefore, it is not possible to precisely perform line-of-sight tracing measurement at the same time with respect to objects that are at different distances in the depth direction, by performing calibration once. Accordingly, in order to find visual behavior of an individual with respect to objects that are at different distances in the depth direction, many man-hours are required for the calibration procedure only.

According to JP 2018-531706A, a measurement result is processed using an appropriate coordinate system as a result of an image capturing device capturing an image of the head of a subject who is gazing in a direction in which an observation target position is observed, and therefore the subject need not wear any device. This reduces a burden on the subject, but the troublesomeness of performing calibration or measurement for objects that are at different distances in the depth direction cannot be solved by merely introducing the image capturing device.

Also, when designing an eyeglass lens (in particular, a progressive power lens), it is important to measure visual behavior with respect to objects that are at different distances in the depth direction, rather than a specific viewing distance only. This is because, if visual behavior of the subject is not within an appropriate range with respect to variation in the additional power of the progressive power lens, the subject has to take an unnatural posture by excessively rotating eyeballs or excessively lowering the chin, for example, and discomfort increases.

An embodiment of the present invention has an object of providing technology with which it is possible to measure visual behavior with respect to objects that are at different distances in the depth direction, while reducing the burden on the subject.

A first aspect of the present invention is a method for measuring visual behavior of a subject to design an eyeglass lens, the method including:

a step (a) of ascertaining a head rotation amount that is generated by the subject in a sagittal plane of the subject when gazing at each of a plurality of gaze points that are set at predetermined distances different from each other in a forward depth direction; and a step (b) of determining an eyeball rotation amount that is generated by the subject when gazing at each of the plurality of gaze points, based on the head rotation amount.

A second aspect of the present invention is the method for measuring visual behavior according to the first aspect, wherein the plurality of gaze points are set in a real space.

A third aspect of the present invention is the method for measuring visual behavior according to the first or the second aspect, wherein the plurality of gaze points are set in a range of 0.25 m or more and 5 m or less in the forward depth direction from the subject.

A fourth aspect of the present invention is the method for measuring visual behavior according to any one of the first to third aspects, wherein, in the step (a), the head rotation amount is ascertained using a sensor that detects a positional change of the head of the subject.

A fifth aspect of the present invention is the method for measuring visual behavior according to any one of the first to fourth aspects, wherein, in the step (a), the subject gazes at the plurality of gaze points in a state of wearing an eyeglass lens for vision correction.

A sixth aspect of the present invention is the method for measuring visual behavior according to the fifth aspect, wherein the eyeglass lens for vision correction is a progressive power lens.

A seventh aspect of the present invention is the method for measuring visual behavior according to the sixth aspect, wherein the plurality of gaze points are each set at a position that satisfies a relationship between an object distance and a line-of-sight direction, the relationship being obtained based on a result of ray tracing performed for the progressive power lens.

An eighth aspect of the present invention is a method for judging visual behavior of a subject to design an eyeglass lens, the method including:
- a step (a) of ascertaining a head rotation amount that is generated by the subject in a sagittal plane of the subject when gazing at each of a plurality of gaze points that are set at predetermined distances different from each other in a forward depth direction;
- a step (b) of determining an eyeball rotation amount that is generated by the subject when gazing at each of the plurality of gaze points, based on the head rotation amount; and
- a step (c) of judging visual behavior of the subject by using the head rotation amount and the eyeball rotation amount, or using the eyeball rotation amount.

A ninth aspect of the present invention is a method for designing a progressive power lens, including:
- a step (a) of ascertaining a head rotation amount that is generated by a subject in a sagittal plane of the subject when gazing at each of a plurality of gaze points that are set at predetermined distances different from each other in a forward depth direction;
- a step (b) of determining an eyeball rotation amount that is generated by the subject when gazing at each of the plurality of gaze points, based on the head rotation amount;
- a step (c) of judging visual behavior of the subject by using the head rotation amount and the eyeball rotation amount, or using the eyeball rotation amount;
- a step (d) of determining a correction method for correcting a progressive power lens based on a result of judgement made in the step (c); and
- a step (e) of correcting a design of the progressive power lens based on the correction method determined in the step (d).

A tenth aspect of the present invention is a method for manufacturing a progressive power lens, including:
- a step (a) of ascertaining a head rotation amount that is generated by a subject in a sagittal plane of the subject when gazing at each of a plurality of gaze points that are set at predetermined distances different from each other in a forward depth direction;
- a step (b) of determining an eyeball rotation amount that is generated by the subject when gazing at each of the plurality of gaze points, based on the head rotation amount;
- a step (c) of judging visual behavior of the subject by using the head rotation amount and the eyeball rotation amount, or using the eyeball rotation amount;
- a step (d) of determining a correction method for correcting a progressive power lens based on a result of judgement made in the step (c);
- a step (e) of correcting a design of the progressive power lens based on the correction method determined in the step (d); and
- a step (f) of processing the progressive power lens based on the design corrected in the step (e).

An eleventh aspect of the present invention is a system for measuring visual behavior, including:
- a head rotation amount ascertainment unit configured to ascertain a head rotation amount that is generated by a subject in a sagittal plane of the subject when gazing at each of a plurality of gaze points that are set at predetermined distances different from each other in a forward depth direction; and
- an eyeball rotation amount ascertainment unit configured to ascertain an eyeball rotation amount that is generated by the subject when gazing at each of the plurality of gaze points, based on the head rotation amount.

A twelfth aspect of the present invention is a system for designing a progressive power lens, including:
- a head rotation amount ascertainment unit configured to ascertain a head rotation amount that is generated by a subject in a sagittal plane of the subject when gazing at each of a plurality of gaze points that are set at predetermined distances different from each other in a forward depth direction;
- an eyeball rotation amount ascertainment unit configured to ascertain an eyeball rotation amount that is generated by the subject when gazing at each of the plurality of gaze points, based on the head rotation amount;
- a judgement unit configured to judge visual behavior of the subject by using the head rotation amount and the eyeball rotation amount, or using the eyeball rotation amount; and
- a correction unit configured to correct a design of a progressive power lens based on a result of judgement made by the judgement unit.

According to an embodiment of the present invention, it is possible to measure visual behavior with respect to objects that are at different distances in the depth direction, while reducing the burden on the subject.

DETAILED DESCRIPTION OF THE INVENTION

The following describes an embodiment of the present invention with reference to the drawings. The present invention is not limited to this example, but is defined by the claims, and is intended to encompass all modifications within the meanings and scope that are equivalent to the claims.

First Embodiment of the Present Invention (1) Method for Measuring Visual Behavior First, a method for measuring visual behavior of a subject 10 to design an eyeglass lens will be described.

Figure 1:
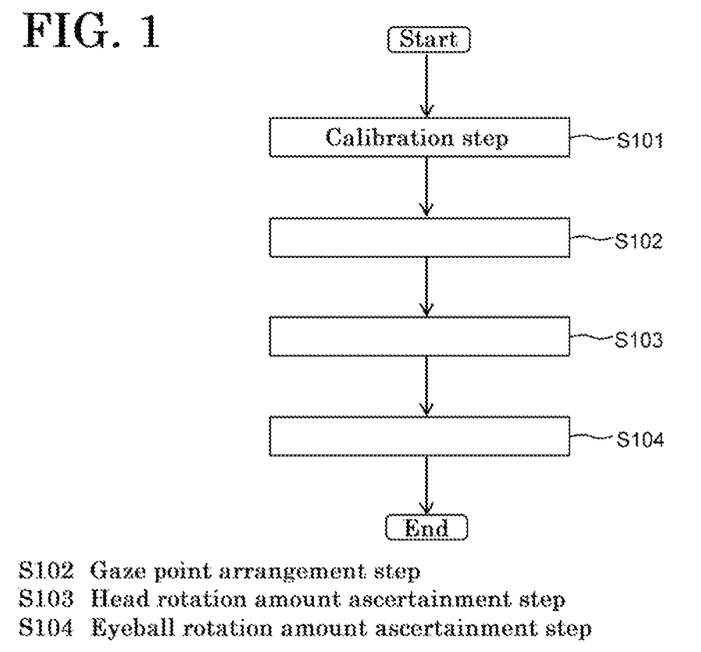
FIG. 1 is a flowchart showing an example of a method for measuring visual behavior according to a first embodiment.

FIG. 1 is a flowchart showing an example of the method for measuring visual behavior according to the present embodiment. As shown in FIG. 1, the method for measuring visual behavior according to the present embodiment includes a calibration step S101, a gaze point arrangement step S102, a head rotation amount ascertainment step S103, and an eyeball rotation amount ascertainment step S104, for example.

In the present specification, rotation of an eyeball means rotation of an eyeball that occurs when a person looks up or down, such as downward rotation (infraversion) of an eyeball referred to in JIS T 7337:2020 Annex JA, for example, rather than movement (torsion) of an eyeball around a rotation axis that is a front-rear axis of the eyeball, and an angle that is generated in a vertical plane, or preferably in the midsagittal plane as a result of this movement will be referred to as an eyeball rotation amount. Also, rotation of the head means upward or downward movement of the head that occurs when a person looks up or down by bending or stretching the neck, and an angle that is generated in a vertical plane, or preferably in the midsagittal plane as a result of the upward or downward tilting of the head will be referred to as a head rotation amount.

Figure 2:
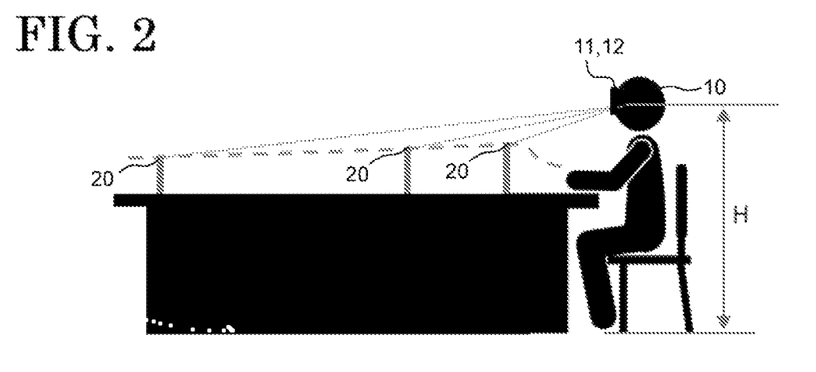
FIG. 2 is a schematic diagram showing an example of a positional relationship between a subject 10 and gaze points 20 according to the first embodiment.

FIG. 2 is a schematic diagram showing an example of a positional relationship between the subject 10 and gaze points 20. The subject 10 is wearing eyeglasses 11 that include progressive power lenses. In the present specification, the subject 10 wearing the eyeglasses 11 or the like that include progressive power lenses will also be simply referred to as the subject 10 wearing progressive power lenses, to avoid redundancy. A sensor 12 is attached to the eyeglasses 11 as a detection unit that detects a positional change of the head of the subject 10. An accelerometer can be used as the sensor 12, for example. The sensor 12 need not necessarily be attached to the eyeglasses 11, and is only required to be disposed at a position at which the sensor 12 can detect a positional change of the head of the subject 10.

In the present specification, the term "progressive power lens" refers to a lens in which the refractive power continuously changes in a part or the entirety of the single lens, and encompasses the refractive power change lens described in JIS T 7337:2020, for example. Progressive power lenses commonly encompass lenses that are called a bifocal lens, a progressive power lens for middle/near vision, a progressive additional lens, an accommodation support lens, or the like.

Calibration Step S101

In the calibration step S101, first, a height H from the floor to the eyes of the subject 10 is measured. Then, the sensor 12 is calibrated such that a posture assumed when the subject 10 horizontally looks far ahead is the reference ($\theta=0°$) for the head rotation amount $\theta$ generated by the subject 10. As a result of this, the head rotation amount $\theta$ can be ascertained accurately in the head rotation amount ascertainment step S103, which will be described later.

In the calibration step S101, the above-described calibration is preferably performed in a state where the subject 10 is horizontally gazing at a visual target for calibration of the height H, which is set far ahead of the subject 10, for example. Also, the visual target for calibration is preferably set at a distance of 2 m or more in the forward depth direction from the subject 10 so that the subject 10 can easily maintain a horizontal line of sight. A black circle printed on a white background can be used as the visual target for calibration, for example.

Gaze Point Arrangement Step S102

In the gaze point arrangement step S102, a plurality of gaze points 20 are set at predetermined distances that differ from each other in the forward depth direction in a sagittal plane of the subject 10. In order to measure visual behavior in detail, the number of gaze points 20 is preferably at least three, and more preferably at least five. Also, the number of gaze points 20 is preferably no greater than ten so as not to increase the burden on the subject 10.

In the present specification, the term "sagittal plane" encompasses not only the midsagittal plane that equally divides the body of the subject 10 into right and left halves along the midline of the subject 10, but also all vertical planes that are parallel to the midsagittal plane and are at distances no greater than half an interpupillary distance PD of the subject 10 from the midsagittal plane, in order to take a change in the posture of the subject 10 in the left-right direction into account.

The plurality of gaze points 20 are preferably set in a real space. In this case, it is possible to measure visual behavior with respect to objects that are at different distances in the depth direction more accurately than in a case where the plurality of gaze points 20 are displayed in a display device such as a tablet to simulatively set visual targets at the different distances in the depth direction. It is preferable to use, as the gaze points 20 set in the real space, visual targets that have appropriate sizes so that the subject 10 can determine whether it is easy or hard to see the visual targets, in a short time (preferably within a few seconds), such as Landolt rings having sizes that correspond to a decimal visual acuity of 0.7 or more at distances from the subject 10 to the gaze points 20, for example. Thus, it is possible to allow the subject 10 to easily assume a posture with which the subject can see the visual targets most clearly when gazing at the gaze points 20.

When states where the subject 10 directs the line of sight to various objects in front of the subject in actual daily life are considered, it is preferable to set the plurality of gaze points 20 in a range of 0.25 m or more and 5 m or less in the forward depth direction from the subject 10 in order to reproduce visual behavior (rotation of the head and rotation of an eyeball) with respect to each object. In the case of a so-called bifocal lens, for example, it is conceivable to set at least one gaze point 20 in a range of 2 m or more and 5 m or less assuming far vision, and set at least one gaze point 20 in a range of 0.25 m or more and 0.5 m or less assuming near vision. By appropriately setting distances to the gaze points 20 according to the type of the progressive power lens worn by the subject as described above, it is possible to measure visual behavior of the subject 10 more accurately with respect to objects that are at different distances in the depth direction.

The plurality of gaze points 20 are each preferably set at a position that satisfies a relationship between an object distance and a line-of-sight direction, which is obtained based on a result of ray tracing performed for the progressive power lens worn by the subject 10. When the subject 10 gazes at each of the gaze points 20 by merely rotating eyeballs without moving the head, a position at which a refractive power D [diopter] at the position on the progressive power lens through which the line of sight passes and a distance L [m] from an eye of the subject 10 to the gaze point 20 (hereinafter also referred to as an "object distance L") satisfy a relationship of D=1/L is determined through the ray tracing, and the gaze point 20 is set at the determined position. As a result of this, the subject 10 can gaze at each of the plurality of gaze points 20 by focusing on the gaze point. In the present specification, if the refractive power at the position through which the line of sight passes differs between left and right progressive power lenses, it is possible to use the refractive power of either one of the left and right progressive power lenses, or use an average value of the refractive powers.

Even if positions that satisfy the relationship of D=1/L are determined and the gaze points 20 are respectively set at the positions as described above, it is envisaged that the subject 10 will assume a posture that involves not only rotation of eyeballs but also rotation of the head when gazing at the gaze points 20. Therefore, a head rotation amount θ that is generated by the subject 10 is ascertained in the head rotation amount ascertainment step S103 described below.

Head Rotation Amount Ascertainment Step S103

In the head rotation amount ascertainment step S103, a head rotation amount θ generated by the subject 10 when gazing at each of the plurality of gaze points 20 is ascertained using the sensor 12. Specifically, a head rotation amount θ generated by the subject 10 is ascertained by letting the subject 10 gaze at the farthest gaze point 20 for 40 seconds in a natural state where both eyes are open, for example. Thereafter, the line of sight is made free for 20 seconds. The above process is performed successively to the nearest gaze point 20. The gaze points 20 need not necessarily be gazed at in the order from the farthest one to the nearest one, and may be gazed at in order from the nearest one to the farthest one.

In the head rotation amount ascertainment step S103, it is possible to use the above-described Landolt rings as the gaze points 20 and let the subject 10 discern directions in which the Landolt rings are open, in order to confirm that the subject 10 can clearly see the gaze points 20.

In the present embodiment, the plurality of gaze points 20 are set in a sagittal plane of the subject 10, and accordingly, it is preferable to consider only rotation in the up-down direction (vertical direction) for the head rotation amount θ generated by the subject 10. In this case, influence of aberration in a side portion of the progressive power lens can be eliminated, for example, and therefore, measurement of the visual behavior can be simplified. In the present specification, the head rotation amount θ is expressed using a positive value in the case of upward rotation, and is expressed using a negative value in the case of downward rotation.

In the head rotation amount ascertainment step S103, it is preferable that the subject 10 gazes at the plurality of gaze points 20 in a state of wearing a progressive power lens. In this case, it is possible to judge whether or not the visual behavior of the subject 10 is within an appropriate range with respect to variation in the additional power of the progressive power lens. Details of the judgement of the visual behavior will be described later.

Eyeball Rotation Amount Ascertainment Step S104

In the eyeball rotation amount ascertainment step S104, an eyeball rotation amount φ that is generated by the subject 10 when gazing at each of the plurality of gaze points 20 is ascertained by determining the eyeball rotation amount φ based on the head rotation amount θ. Thus, it is possible to measure visual behavior of the subject 10 with respect to objects that are at different distances in the depth direction.

In the eyeball rotation amount ascertainment step S104, the eyeball rotation amount φ is preferably determined based on the assumption that a line-of-sight direction (angle) when gazing at each of the plurality of gaze points 20 is realized by a sum of the head rotation amount θ and the eyeball rotation amount φ. In this case, the eyeball rotation amount φ can be determined without using a device for measuring movement of eyeballs of the subject 10, and accordingly, the burden on the subject 10 can be reduced.

Similarly to the head rotation amount θ, it is preferable to consider only rotation in the up-down direction (vertical direction) for the eyeball rotation amount φ generated by the subject 10. In the present specification, the eyeball rotation amount φ is expressed using a positive value in the case of upward rotation, and is expressed using a negative value in the case of downward rotation.

Through the steps described above, it is possible to measure visual behavior with respect to objects that are at different distances in the depth direction while reducing the burden on the subject 10. In order to design an eyeglass lens (in particular, a progressive power lens), it is important to measure visual behavior with respect to objects that are at different distances in the depth direction, rather than a specific viewing distance only. This is because, if the visual behavior of the subject 10 is not within an appropriate range with respect to variation in the additional power of the progressive power lens, the subject 10 has to assume an unnatural posture by excessively rotating eyeballs or excessively lowering the chin, for example, and discomfort increases. It is possible to design a progressive power lens that is appropriate for the visual behavior of the subject 10 by considering the visual behavior measured according to the present embodiment.

(2) Method for Judging Visual Behavior

Next, a method for judging visual behavior of the subject 10 to design an eyeglass lens will be described.

Figure 3:
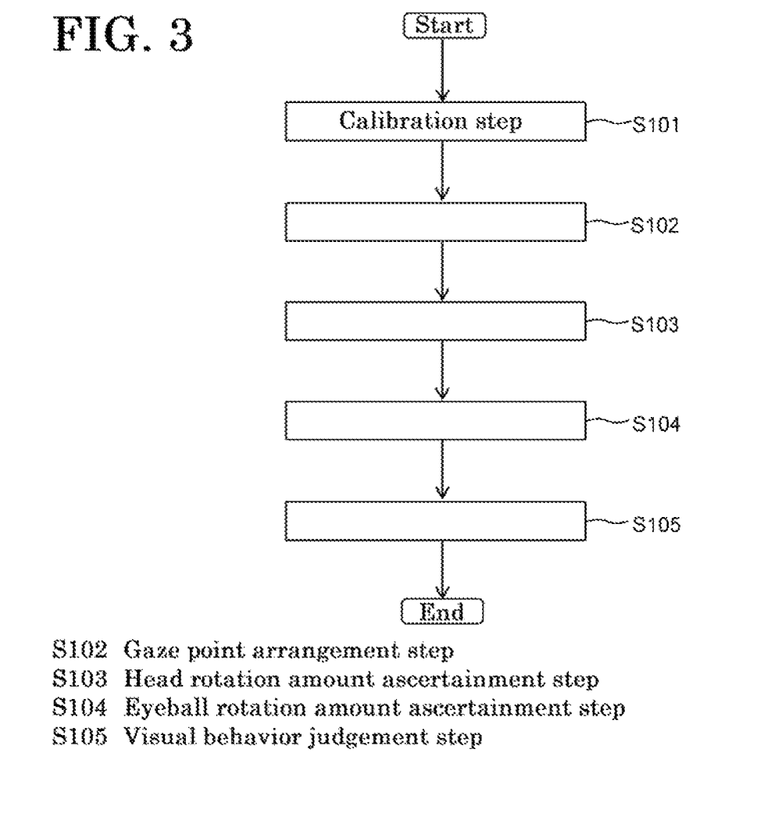
FIG. 3 is a flowchart showing an example of a method for judging visual behavior according to the first embodiment.

FIG. 3 is a flowchart showing an example of the method for judging visual behavior according to the present embodiment. As shown in FIG. 3, the method for judging visual behavior according to the present embodiment includes the calibration step S101, the gaze point arrangement step S102, the head rotation amount ascertainment step S103, the eyeball rotation amount ascertainment step S104, and a visual behavior judgement step S105, for example. The steps other than the visual behavior judgement step S105 can be performed as described above in (1) Method for measuring visual behavior, and therefore, descriptions thereof are omitted.

Visual Behavior Judgement Step S105

In the visual behavior judgement step S105, visual behavior of the subject 10 is judged using the head rotation amount θ and the eyeball rotation amount φ. Thus, it is possible to judge whether or not the visual behavior of the subject 10 is within an appropriate range with respect to variation in the additional power of the progressive power lens.

Figure 4:
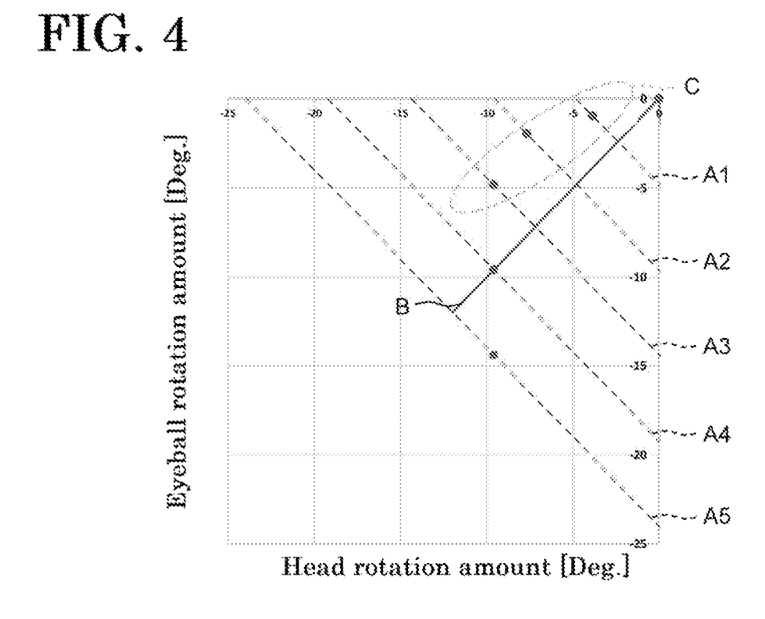
FIG. 4 is a graph showing an example of a plot of head rotation amounts $\theta$ and eyeball rotation amounts $\varphi$ according to the first embodiment.

FIG. 4 is a graph showing an example of a plot of the head rotation amount θ and the eyeball rotation amount φ. In FIG. 4, the horizontal axis indicates the head rotation amount θ, and the vertical axis indicates the eyeball rotation amount φ. Measurement points plotted in the graph indicate head rotation amounts θ and eyeball rotation amounts φ ascertained for the plurality of gaze points 20, and each measurement point corresponds to a measurement result obtained for a single gaze point 20. The sum of the head rotation amount θ and the eyeball rotation amount φ is constant on each of additional lines (A1 to A5) extending downward to the right, and the ordinate intercept of each of the additional lines (A1 to A5) indicates an eyeball rotation amount $\varphi$ of a case where the subject 10 gazes at a gaze point 20 by merely rotating eyeballs without moving the head. That is, in the case where eyeball rotation amounts $\varphi$ are determined in the eyeball rotation amount ascertainment step S104 based on the assumption that a line-of-sight direction (angle) when gazing at each of the plurality of gaze points 20 is realized by the sum of the head rotation amount $\theta$ and the eyeball rotation amount $\varphi$, measurement points are plotted on the additional lines (A1 to A5).

In FIG. 4, an additional line B extending upward to the right indicates that a ratio between the head rotation amount $\theta$ and the eyeball rotation amount $\varphi$ is 1:1 on this line. This means that the absolute value of the head rotation amount $\theta$ is greater than the absolute value of the eyeball rotation amount $\varphi$ at each measurement point that is on the upper left of the additional line B, and the absolute value of the eyeball rotation amount $\varphi$ is greater than the absolute value of the head rotation amount $\theta$ at each measurement point that is on the lower right of the additional line B.

A judgement condition in the visual behavior judgement step S105 is, for example, that the absolute value of the head rotation amount $\theta$ is no greater than the absolute value of the eyeball rotation amount $\varphi$, in a case where both the head rotation amount $\theta$ and the eyeball rotation amount $\varphi$ are negative values. This is because, if the absolute value of the head rotation amount $\theta$ is greater than the absolute value of the eyeball rotation amount $\varphi$, there is a possibility that the variation in the additional power of the progressive power lens is not used effectively. In FIG. 4, three measurement points that are surrounded by a dashed line C do not satisfy the judgement condition. The judgement condition in the visual behavior judgement step S105 may be changed as necessary, or a plurality of judgement conditions may also be set. That is, the visual behavior judgement step S105 can be performed by obtaining numerical values that are necessary for the judgement from among the head rotation amount $\theta$, the eyeball rotation amount $\varphi$, trends of variation in these values with respect to the gaze points 20, a ratio between these values, and the like, and by performing analysis.

In the visual behavior judgement step S105, the visual behavior of the subject 10 is judged inappropriate in a case where more than 40% (preferably more than 20%, and more preferably at least one) of the plurality of measurement points do not satisfy the judgement condition, for example. That is, it is determined that the visual behavior of the subject 10 is not within an appropriate range with respect to the variation in the additional power of the progressive power lens and there is a possibility that the subject 10 cannot use the progressive power lens comfortably. In this case, the design of the progressive power lens may be changed such that a larger number of measurement points satisfy the judgement condition, for example.

Alternatively, in the visual behavior judgement step S105, it is also possible to judge the visual behavior of the subject 10 inappropriate in a case where a measurement point largely deviates from a trend of the visual behavior of the subject 10, for example. More specifically, it is also possible to find a regression line for the plurality of measurement points using the least squares method, and judge the visual behavior of the subject 10 inappropriate in a case where there is a measurement point for which an error from the regression line is greater than a predetermined value, for example. In this case, it is also possible to design the progressive power lens so as to change the additional power in a region of the progressive power lens that corresponds to the measurement point for which the error is greater than the predetermined value, for example. If the progressive power lens is designed as described above, it is expected that the subject 10 will be able to use the progressive power lens with more natural visual behavior.

In the visual behavior judgement step S105, the visual behavior of the subject 10 is judged appropriate in a case where 60% or more (preferably 80% or more, and more preferably 100%) of the plurality of measurement points satisfy the judgement condition, for example. That is, it is determined that the visual behavior of the subject 10 is within an appropriate range with respect to the variation in the additional power of the progressive power lens and the subject 10 can use the progressive power lens comfortably.

(3) Method for Designing Progressive Power Lens and Method for Manufacturing Progressive Power Lens Next, a method for designing a progressive power lens and a method for manufacturing a progressive power lens will be described.

Figure 5:
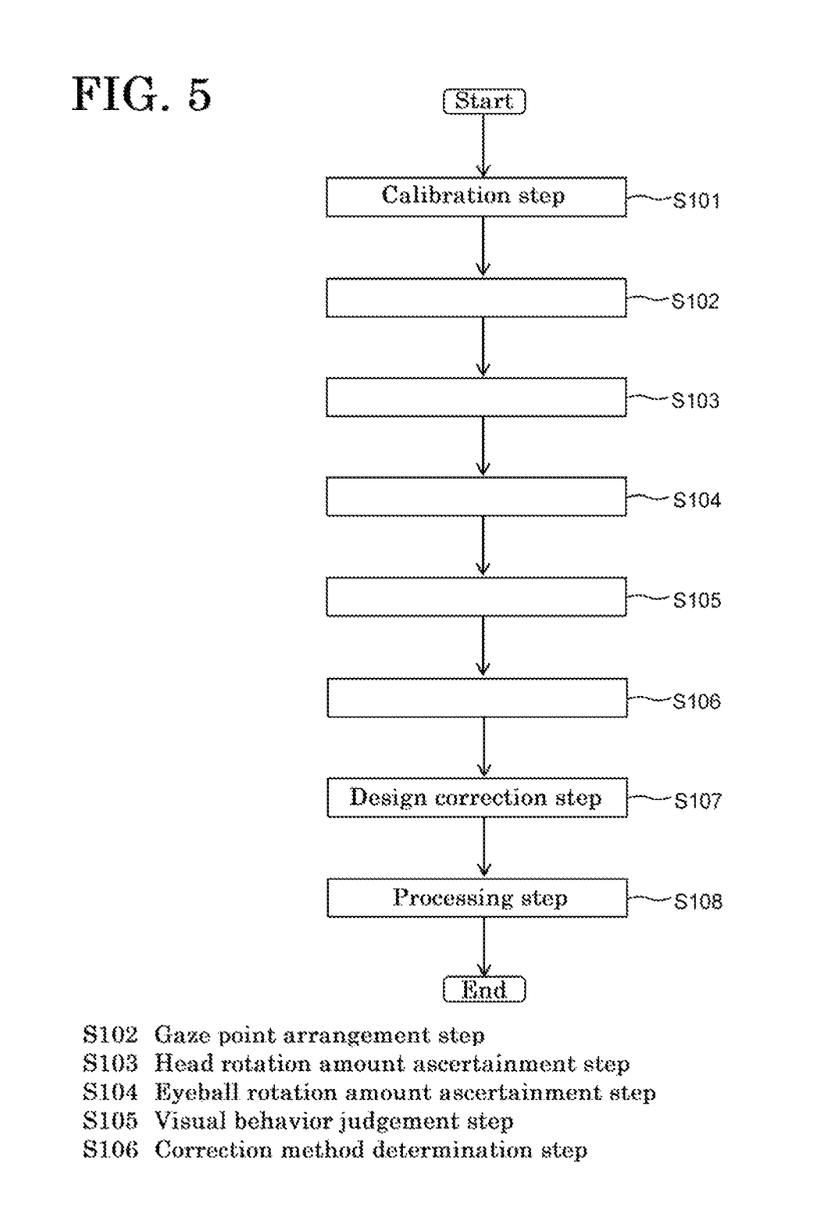
FIG. 5 is a flowchart showing an example of a method for manufacturing a progressive power lens according to the first embodiment.

FIG. 5 is a flowchart showing an example of the method for manufacturing a progressive power lens according to the present embodiment. As shown in FIG. 5, the method for manufacturing a progressive power lens according to the present embodiment includes the calibration step S101, the gaze point arrangement step S102, the head rotation amount ascertainment step S103, the eyeball rotation amount ascertainment step S104, the visual behavior judgement step S105, a correction method determination step S106, a design correction step S107, and a processing step S108, for example. The steps other than the correction method determination step S106, the design correction step S107, and the processing step S108 can be performed as described above in (1) Method for measuring visual behavior and (2) Method for judging visual behavior, and therefore, descriptions thereof are omitted.

Correction Method Determination Step S106

In the correction method determination step S106, a correction method for correcting the progressive power lens is determined based on a result of judgement made in the visual behavior judgement step S105. Specifically, the correction method for correcting the progressive power lens is determined such that a larger number of measurement points satisfy the judgement condition in the visual behavior judgement step S105, for example.

In the correction method determination step S106, the correction method is determined so as to change the additional power in a region of the progressive power lens that corresponds to a measurement point that does not satisfy the judgement condition in the visual behavior judgement step S105, for example. Alternatively, in the correction method determination step S106, it is also possible to determine a correction method that includes correction of at least one of a progressive change start point and a progressive change end point of the progressive power lens, for example.

Design Correction Step S107

In the design correction step S107, the design of the progressive power lens is corrected based on the correction method determined in the correction method determination step S106. Thus, it is possible to design a progressive power lens that is appropriate for the visual behavior of the subject 10.

In the present embodiment, the processing step S108 may be omitted. In this case, the progressive power lens appropriate for the visual behavior of the subject 10 can be designed through the steps described above. That is, the method for manufacturing a progressive power lens according to the present embodiment can also be performed as a method for designing a progressive power lens.

Processing Step S108

In the processing step S108, the progressive power lens is processed based on the design corrected in the design correction step S107. Thus, it is possible to manufacture a progressive power lens that is appropriate for the visual behavior of the subject 10.

(4) Visual Behavior Measurement System

Next, a visual behavior measurement system 100 according to the present embodiment will be described.

Figure 6:
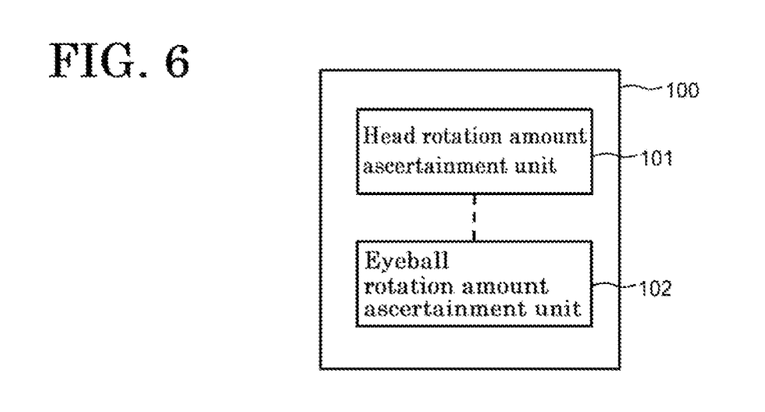
FIG. 6 is a block diagram showing a schematic configuration of a visual behavior measurement system 100 according to the first embodiment.

FIG. 6 is a block diagram showing a schematic configuration of the visual behavior measurement system 100 according to the present embodiment. As shown in FIG. 6, the visual behavior measurement system 100 according to the present embodiment includes a head rotation amount ascertainment unit 101 and an eyeball rotation amount ascertainment unit 102, for example. The visual behavior measurement system 100 is configured to measure visual behavior of the subject 10 in order to design an eyeglass lens, and is installed in a factory of an eyeglass lens manufacturer, for example.

The head rotation amount ascertainment unit 101 is configured to ascertain a head rotation amount θ generated by the subject 10 in a sagittal plane of the subject 10 when the subject 10 gazes at each of the plurality of gaze points 20 that are set at predetermined distances that differ from each other in the forward depth direction. The head rotation amount ascertainment unit 101 is configured to ascertain head rotation amounts θ for the respective gaze points 20, which are obtained in the head rotation amount ascertainment step S103 described above, for example. A computer that executes a predetermined program as necessary can be used as the head rotation amount ascertainment unit 101, for example.

The eyeball rotation amount ascertainment unit 102 is configured to ascertain an eyeball rotation amount φ generated by the subject 10 when the subject 10 gazes at each of the plurality of gaze points 20, based on the head rotation amount θ ascertained by the head rotation amount ascertainment unit 101. The eyeball rotation amount ascertainment unit 102 is configured to ascertain eyeball rotation amounts φ for the respective gaze points 20, which are obtained in the eyeball rotation amount ascertainment step S104 described above, for example. A computer that executes a predetermined program as necessary can be used as the eyeball rotation amount ascertainment unit 102, for example.

The head rotation amount ascertainment unit 101 and the eyeball rotation amount ascertainment unit 102 may be connected to each other via a network, or may be provided in the same computer.

It is possible to design a progressive power lens that is appropriate for the visual behavior of the subject 10 by considering visual behavior measured using the visual behavior measurement system 100 configured as described above.

(5) Progressive Power Lens Design System

Next, a progressive power lens design system 200 according to the present embodiment will be described.

Figure 7:
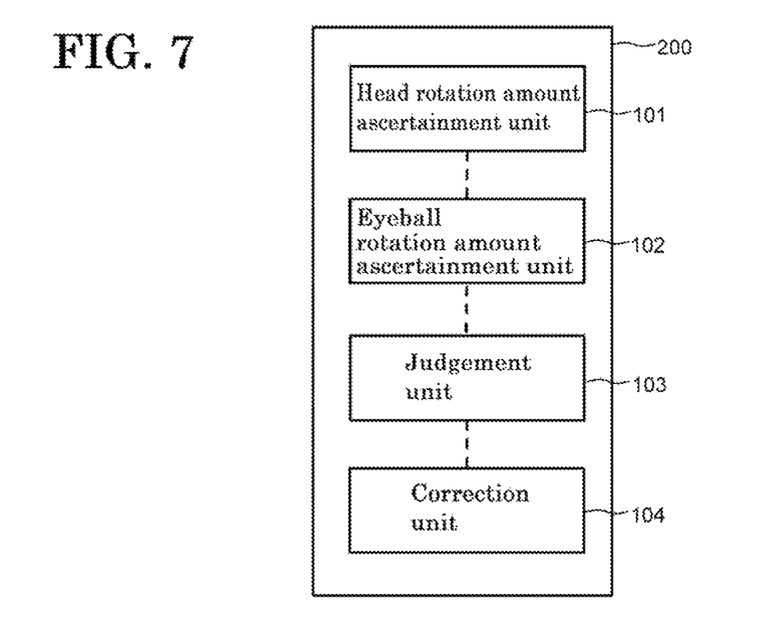
FIG. 7 is a block diagram showing a schematic configuration of a progressive power lens design system 200 according to the first embodiment.

FIG. 7 is a block diagram showing a schematic configuration of the progressive power lens design system 200 according to the present embodiment. As shown in FIG. 7, the progressive power lens design system 200 according to the present embodiment includes the head rotation amount ascertainment unit 101, the eyeball rotation amount ascertainment unit 102, a judgement unit 103, and a correction unit 104, for example. The progressive power lens design system 200 is configured to design a progressive power lens, and is installed in a factory of an eyeglass lens manufacturer, for example. The head rotation amount ascertainment unit 101 and the eyeball rotation amount ascertainment unit 102 are the same as those described above in (4) Visual behavior measurement system, and therefore, descriptions thereof are omitted.

The judgement unit 103 is configured to judge the visual behavior of the subject 10 using the head rotation amount θ ascertained by the head rotation amount ascertainment unit 101 and the eyeball rotation amount φ ascertained by the eyeball rotation amount ascertainment unit 102. The judgement unit 103 can use the judgement condition described above regarding the visual behavior judgement step S105 to judge the visual behavior. A computer that executes a predetermined program as necessary can be used as the judgement unit 103, for example.

The correction unit 104 is configured to correct the design of the progressive power lens based on a result of judgement made by the judgement unit 103. A computer that executes a predetermined program as necessary can be used as the correction unit 104, for example.

The head rotation amount ascertainment unit 101, the eyeball rotation amount ascertainment unit 102, the judgement unit 103, and the correction unit 104 may be connected to each other via a network, or may be provided in the same computer.

It is possible to design a progressive power lens that is appropriate for the visual behavior of the subject 10 by using the progressive power lens design system 200 configured as described above.

Other Embodiments of the Present Invention

Although an embodiment of the present invention has been specifically described, the present invention is not limited to the embodiment described above, and various changes can be made within a scope not departing from the gist of the present invention.

For example, in the above-described embodiment, an explanation is given for the case where the visual behavior is measured in a state where the subject 10 is wearing the progressive power lens, but the visual behavior may also be measured in a state where the subject 10 is wearing an eyeglass lens for vision correction (e.g., a fixed focal lens) other than the progressive power lens or the subject 10 is not wearing an eyeglass lens. In such a case as well, it is possible to design a progressive power lens appropriate for the visual behavior of the subject 10 similarly to the above-described embodiment by measuring the visual behavior in a state where the subject 10 is not wearing the progressive power lens (i.e., in a state where the refractive power of the eyeglass lens does not vary depending on the line-of-sight direction).

In the above-described embodiment, an explanation is given for the case where the eyeball rotation amount φ is determined in the eyeball rotation amount ascertainment step S104 based on the assumption that a line-of-sight direction (angle) when gazing at each of the plurality of gaze points 20 is realized by the sum of the head rotation amount θ and the eyeball rotation amount φ, but it is also possible to attach a sensor 12 to the position of the hip or the neck of the subject 10 and determine the eyeball rotation amount φ taking movement of the hip or the neck of the subject 10 into account, for example. It is possible to measure the visual behavior more accurately by using the plurality of sensors 12 to detect a change in the posture when the subject 10 gazes at the gaze points 20.

It is also possible to measure the visual behavior according to the above-described embodiment a plurality of times by letting the subject 10 wear a plurality of progressive power lenses of different designs, for example. In this case, an eyeglass lens may be designed using an average value of visual behaviors (head rotation amounts $\theta$ and eyeball rotation amounts $\varphi$) obtained through the measurement performed the plurality of times, or using the most natural visual behavior (e.g., the absolute value of the head rotation amount $\theta$ is the smallest) among visual behaviors obtained through the measurement performed the plurality of times.

In the above-described embodiment, an explanation is given for the case where the head rotation amount $\theta$ of the subject 10 is ascertained using the sensor 12, but the detection unit for detecting a positional change of the head of the subject 10 is not limited to the sensor 12. Specifically, a head image capturing device may be disposed as the detection unit on a side of the subject 10, for example. In this case, the head rotation amount $\theta$ can be ascertained similarly to the above-described embodiment by capturing an image of the head of the subject 10 using the head image capturing device, and analyzing the captured image in the head rotation amount ascertainment step S103. A digital camera that includes a stroboscopic light emission device, an imaging element, an image memory, a computer for performing image processing, and the like can be used as the head image capturing device, for example.

In the above-described embodiment, an explanation is given for the case where the visual behavior of the subject 10 is judged using the head rotation amount $\theta$ and the eyeball rotation amount $\varphi$ in the visual behavior judgement step S105, but the visual behavior of the subject 10 may be judged using only the eyeball rotation amount $\varphi$ in the visual behavior judgement step S105. In this case, a configuration is also possible in which the judgement condition is that the eyeball rotation amount $\varphi$ is within a predetermined range, for example, and when the eyeball rotation amount $\varphi$ exceeds the predetermined range, it is determined that there is a possibility that the subject 10 cannot use the progressive power lens comfortably.

EXAMPLES

Next, examples according to the present invention will be described. These examples are merely examples of the present invention, and the present invention is not limited by these examples.

Example 1

Visual behavior was measured using the method according to the first embodiment described above, letting a subject 10 wear a progressive power lens of a known design. Results are shown in FIG. 8.

Figure 8:
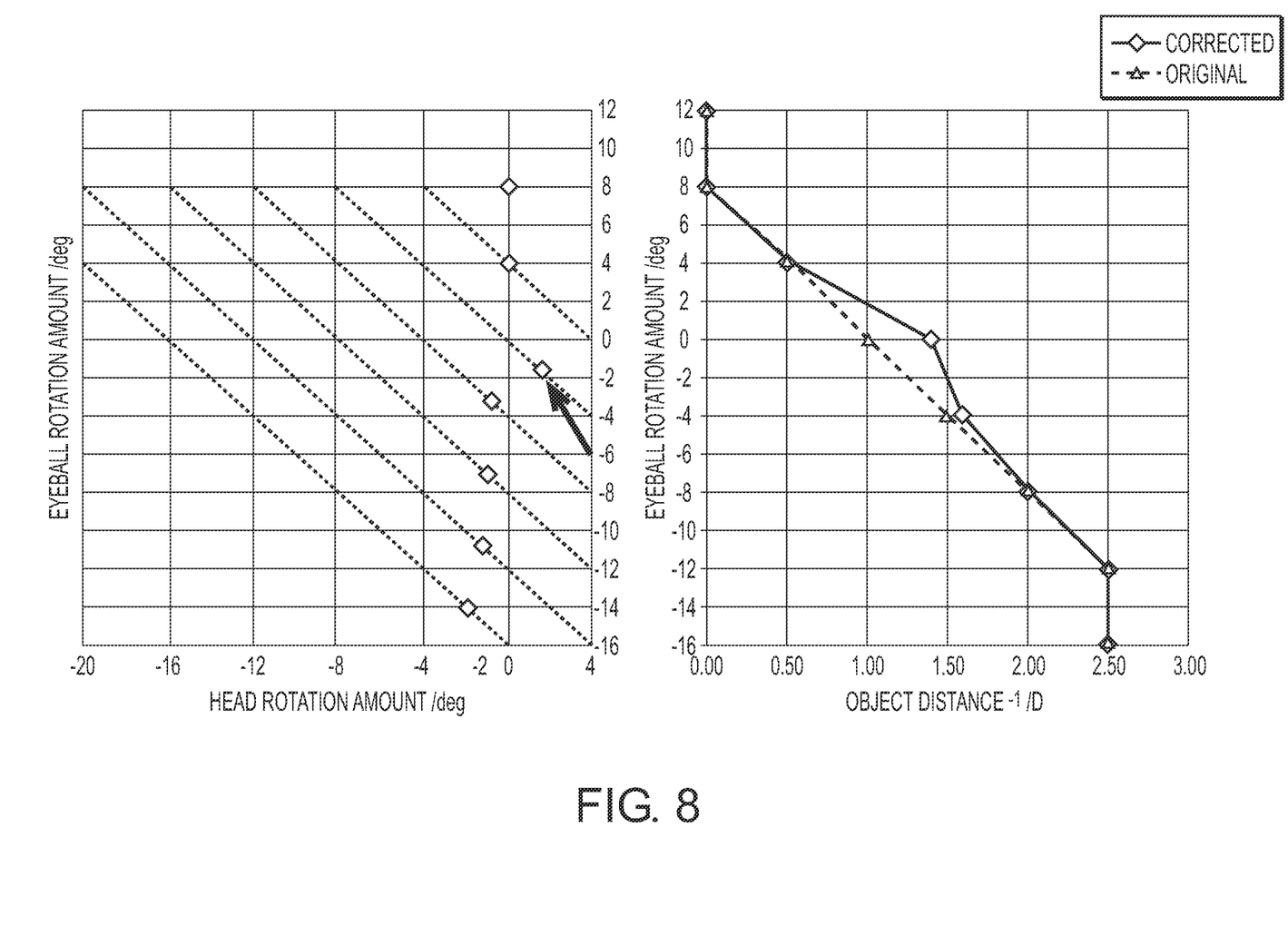
FIG. 8 is a graph showing a measurement result of visual behavior in Example 1.

In FIG. 8, lens power in the right graph indicates variation in the additional power along a main gaze line of the progressive power lens. The left graph shows head rotation amounts $\theta$ and eyeball rotation amounts $\varphi$ for the plurality of gaze points 20. As shown in the left graph of FIG. 8, at the measurement point indicated by an arrow in the graph, the head rotation amount $\theta$ was a positive value and the eyeball rotation amount $\varphi$ was a negative value. This means that in the vicinity of a measurement point that corresponds to a straight forward view (y=0), the subject 10 unnecessarily raised his chin and the position on the progressive power lens through which the line of sight passed was lowered.

Therefore, the progressive power lens was designed so as to increase the additional power in a region (the vicinity of y=0 in the right graph) of the progressive power lens corresponding to the measurement point indicated by the arrow so that the subject would not raise his chin unnecessarily. That is, the variation in the additional power was corrected as shown by the graph denoted with "Corrected" in the right graph. It is expected that the subject 10 can use the progressive power lens with more natural visual behavior as a result of the lens being designed as described above.

Through the above, it was confirmed that a progressive power lens appropriate for the visual behavior of the subject 10 could be designed by measuring the visual behavior of the subject 10 with respect to objects that were at different distances in the depth direction. In particular, it was confirmed that a progressive power lens appropriate for the visual behavior of the subject 10 could be designed in the case where the subject 10 unnecessarily raised his chin and the position on the progressive power lens through which the line of sight passed was lowered.

Example 2

Visual behavior was measured using the method according to the first embodiment described above, letting a subject 10 different from the subject in Example 1 wear a progressive power lens of a known design. Results are shown in FIG. 9.

Figure 9:
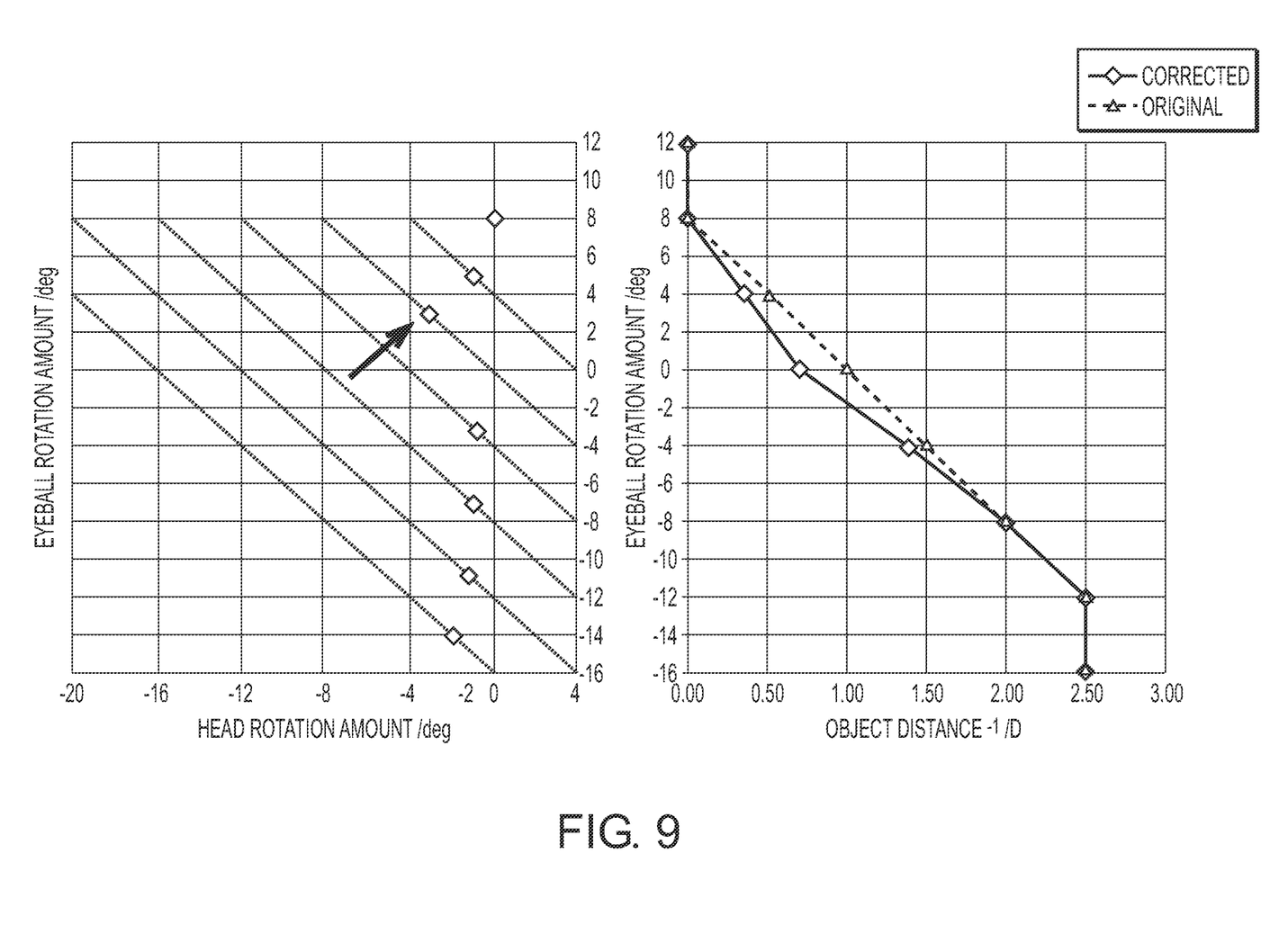
FIG. 9 is a graph showing a measurement result of visual behavior in Example 2.

In FIG. 9, lens power in the right graph indicates variation in the additional power along a main gaze line of the progressive power lens. The left graph shows head rotation amounts $\theta$ and eyeball rotation amounts $\varphi$ for the plurality of gaze points 20. As shown in the left graph of FIG. 9, at the measurement point indicated by an arrow in the graph, the head rotation amount $\theta$ was a negative value and the eyeball rotation amount $\varphi$ was a positive value. This means that in the vicinity of a measurement point corresponding to a straight forward view (y=0), the subject 10 unnecessarily lowered his chin and the position on the progressive power lens through which the line of sight passed was raised.

Therefore, the progressive power lens was designed so as to reduce the additional power in a region (the vicinity of y=0 in the right graph) of the progressive power lens corresponding to the measurement point indicated by the arrow so that the subject would not lower his chin unnecessarily. That is, the variation in the additional power was corrected as shown by the graph denoted with "Corrected" in the right graph. It is expected that the subject 10 can use the progressive power lens with more natural visual behavior as a result of the lens being designed as described above.

Through the above, it was confirmed that a progressive power lens appropriate for the visual behavior of the subject 10 could be designed by measuring the visual behavior of the subject 10 with respect to objects that were at different distances in the depth direction. In particular, it was confirmed that a progressive power lens appropriate for the visual behavior of the subject 10 could be designed in the case where the subject 10 unnecessarily lowered his chin and the position on the progressive power lens through which the line of sight passed was raised.

LIST OF REFERENCE NUMERALS

10 Subject
11 Eyeglasses

12 Sensor
20 Gaze point
100 Measurement system
101 Head rotation amount ascertainment unit
102 Eyeball rotation amount ascertainment unit
103 Judgement unit
104 Correction unit
200 Design system
S101 Calibration step
S102 Gaze point arrangement step
S103 Head rotation amount ascertainment step
S104 Eyeball rotation amount ascertainment step
S105 Visual behavior judgement step
S106 Correction method determination step
S107 Design correction step
S108 Processing step

What is claimed is:

1. A method for measuring visual behavior of a subject to design an eyeglass lens, the method comprising:
    a step (a) of ascertaining a head rotation amount that is generated by the subject in a sagittal plane of the subject when gazing at each of a plurality of gaze points that are set at predetermined and known distances different from each other in a forward depth direction with respect to the subject; and
    a step (b) of determining an eyeball rotation amount that is generated by the subject when gazing at each of the plurality of gaze points, based on an assumption that a line-of-sight angle from the subject's eyes to the plurality of gaze points when the subject is gazing at each of the plurality of gaze points is equal to a sum of the head rotation amount and the eyeball rotation amount, wherein the number of gaze points is at least three.

2. The method for measuring visual behavior according to claim 1,
    wherein the plurality of gaze points are set in a real space.

3. The method for measuring visual behavior according to claim 1,
    wherein the plurality of gaze points are set in a range of 0.25 m or more and 5 m or less in the forward depth direction from the subject.

4. The method for measuring visual behavior according to claim 1,
    wherein, in the step (a), the head rotation amount is ascertained using a sensor that detects a positional change of the head of the subject.

5. The method for measuring visual behavior according to claim 1,
    wherein, in the step (a), the subject gazes at the plurality of gaze points in a state of wearing an eyeglass lens for vision correction.

6. The method for measuring visual behavior according to claim 5,
    wherein the eyeglass lens for vision correction is a progressive power lens.

7. The method for measuring visual behavior according to claim 6,
    wherein the plurality of gaze points are each set at a position that satisfies a relationship between an object distance and a line-of-sight direction, the relationship being obtained based on a result of ray tracing performed for the progressive power lens.

8. A method for designing a progressive power lens, comprising:
    a step (a) of ascertaining a head rotation amount that is generated by a subject in a sagittal plane of the subject when gazing at each of a plurality of gaze points that are set at predetermined and known distances different from each other in a forward depth direction with respect to the subject;
    a step (b) of determining an eyeball rotation amount that is generated by the subject when gazing at each of the plurality of gaze points, based on an assumption that a line-of-sight angle from the subject's eyes to the plurality of gaze points when the subject is gazing at each of the plurality of gaze points is equal to a sum of the head rotation amount and the eyeball rotation amount, the number of gaze points being at least three;
    a step (c) of judging visual behavior of the subject by using the head rotation amount and the eyeball rotation amount, or using the eyeball rotation amount;
    a step (d) of determining a correction method for correcting a progressive power lens based on a result of judgement made in the step (c); and
    a step (e) of correcting a design of the progressive power lens based on the correction method determined in the step (d).

9. A method for manufacturing a progressive power lens, comprising:
    a step (a) of ascertaining a head rotation amount that is generated by a subject in a sagittal plane of the subject when gazing at each of a plurality of gaze points that are set at predetermined and known distances different from each other in a forward depth direction with respect to the subject;
    a step (b) of determining an eyeball rotation amount that is generated by the subject when gazing at each of the plurality of gaze points, based on an assumption that a line-of-sight angle from the subject's eyes to the plurality of gaze points when the subject is gazing at each of the plurality of gaze points is equal to a sum of the head rotation amount and the eyeball rotation amount, the number of gaze points being at least three;
    a step (c) of judging visual behavior of the subject by using the head rotation amount and the eyeball rotation amount, or using the eyeball rotation amount;
    a step (d) of determining a correction method for correcting a progressive power lens based on a result of judgement made in the step (c);
    a step (e) of correcting a design of the progressive power lens based on the correction method determined in the step (d); and
    a step (f) of processing the progressive power lens based on the design corrected in the step (e).

* * * * *